United States Patent
Humphris

(10) Patent No.: US 9,739,798 B2
(45) Date of Patent: *Aug. 22, 2017

(54) MULTIPLE PROBE DETECTION AND ACTUATION

(71) Applicant: INFINITESIMA LIMITED, Oxford, Oxfordshire (GB)

(72) Inventor: Andrew Humphris, Abingdon (GB)

(73) Assignee: INFINITESIMA LIMITED, Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,642

(22) PCT Filed: Aug. 28, 2013

(86) PCT No.: PCT/GB2013/052256
§ 371 (c)(1),
(2) Date: Feb. 27, 2015

(87) PCT Pub. No.: WO2014/033451
PCT Pub. Date: Mar. 6, 2014

(65) Prior Publication Data
US 2015/0219686 A1 Aug. 6, 2015

(30) Foreign Application Priority Data
Aug. 31, 2012 (GB) .................................. 1215546.1

(51) Int. Cl.
*G01Q 20/02* (2010.01)
*B82Y 35/00* (2011.01)
(Continued)

(52) U.S. Cl.
CPC .............. *G01Q 20/02* (2013.01); *B82Y 35/00* (2013.01); *G01B 9/02015* (2013.01);
(Continued)

(58) Field of Classification Search
CPC ................................ G01Q 20/00; G01Q 20/02
(Continued)

(56) References Cited

U.S. PATENT DOCUMENTS 5,047,633 A 9/1991 Finlan et al.
5,144,150 A 9/1992 Yoshizumi et al.
(Continued)

FOREIGN PATENT DOCUMENTS

EP 0397416 A1 11/1990
EP 1892727 A1 2/2008
(Continued)

OTHER PUBLICATIONS

Lavrik, Nikolyay V., et al., "Femtogram Mass Detection Using Photothermally Actuated Nanomechanical Resonators", Applied Physics Letters, pp. 2697-2699, vol. 82, No. 16, Apr. 21, 2003.
(Continued)

*Primary Examiner* — Jason McCormack
(74) *Attorney, Agent, or Firm* — Hauptman Ham, LLP

(57) ABSTRACT

A method of detecting the positions of a plurality of probes. An input beam is directed into an optical device and transformed into a plurality of output beamlets which are not parallel with each other. Each output beamlet is split into a sensing beamlet and an associated reference beamlet. Each of the sensing beamlets is directed onto an associated one of the probes with an objective lens to generate a reflected beamlet which is combined with its associated reference beamlet to generate an interferogram. Each interferogram is measured to determine the position of an associated one of the probes. A similar method is used to actuate a plurality of probes. A scanning motion is generated between the probes and the sample. An input beam is directed into an optical device and transformed into a plurality of actuation beamlets which are not parallel with each other.

16 Claims, 7 Drawing Sheets

(51) Int. Cl.
*G01Q 10/04* (2010.01)
*G01Q 70/06* (2010.01)
*G11B 9/14* (2006.01)
*G11B 11/00* (2006.01)
*G01B 9/02* (2006.01)
*G03F 7/20* (2006.01)
*G03F 1/82* (2012.01)
*G03F 7/00* (2006.01)

(52) U.S. Cl.
CPC .......... *G01Q 10/045* (2013.01); *G01Q 70/06* (2013.01); *G11B 9/14* (2013.01); *G11B 11/002* (2013.01); *G01N 2291/0256* (2013.01); *G01N 2291/106* (2013.01); *G03F 1/82* (2013.01); *G03F 7/0002* (2013.01); *G03F 7/2049* (2013.01); *G11B 9/1445* (2013.01)

(58) Field of Classification Search
USPC .............................. 850/1, 5, 6, 8, 22, 38, 55
See application file for complete search history.

(56) References Cited

U.S. PATENT DOCUMENTS

| | | | | |
|---|---|---|---|---|
| 5,260,824 | A * | 11/1993 | Okada | B82Y 35/00 359/368 |
| 5,485,231 | A * | 1/1996 | Hayashi | A61B 3/028 351/239 |
| 5,760,755 | A * | 6/1998 | Engle | G02B 26/02 345/84 |
| 6,469,293 | B1 * | 10/2002 | Shimizu | B82Y 35/00 250/234 |
| 6,678,056 | B2 | 1/2004 | Downs | |
| 6,779,387 | B2 * | 8/2004 | Degertekin | B82Y 35/00 73/105 |
| 6,884,981 | B2 | 4/2005 | Proksch et al. | |
| 7,084,384 | B2 | 8/2006 | Proksch et al. | |
| 9,389,243 | B2 * | 7/2016 | Humphris | G01Q 10/045 |
| 2003/0047675 | A1 | 3/2003 | Proksch et al. | |
| 2004/0090194 | A1 * | 5/2004 | Gesley | B82Y 10/00 315/500 |
| 2005/0097944 | A1 | 5/2005 | Hare et al. | |
| 2006/0284774 | A1 * | 12/2006 | Salsman | G01R 23/163 343/703 |
| 2008/0047335 | A1 | 2/2008 | Kawasaki et al. | |
| 2009/0313729 | A1 * | 12/2009 | Ando | G01Q 10/065 850/33 |
| 2010/0186132 | A1 * | 7/2010 | Humphris | G01Q 70/06 850/1 |
| 2011/0247106 | A1 | 10/2011 | Humphris | |
| 2012/0007585 | A1 | 1/2012 | Salsman et al. | |
| 2014/0147337 | A1 | 5/2014 | Urey et al. | |

FOREIGN PATENT DOCUMENTS

| | | |
|---|---|---|
| WO | 03/019241 A2 | 3/2003 |
| WO | 2006/055961 A2 | 5/2006 |
| WO | 2010067129 A1 | 6/2010 |
| WO | 2012059828 A2 | 5/2012 |

OTHER PUBLICATIONS

Gibson, Graham M. et al., "Measuring the Accuracy of Particle Position and Force in Optical Tweezers Using High-Speed Video Microscopy", Optics Express, pp. 14561-14570, vol. 16, No. 19 Sep. 15, 2008.

Minne, S.C. et al., "Parallel Atomic Force Micorscopy Using Cantilevers with Integrated Piezoresistive Sensors and Integrated Piezoeletric Actuators", Appl. Phys. Lett., pp. 3918-3920, 67 (26), Dec. 25, 1995.

Ul-Haq, Ehtsham, et A., "The Snomipede: A Parallel Platform for Scanning Near-Field Photolithography", J. Mater. Res., pp. 2997-3008, vol. 26, No. 24, Dec. 28, 2011.

Stockley, J. et al., "Liquid Crystal Spatial Light Modulator for Multispot Beam Steering", SPIE Proceeding, vol. 5160.

Yamashita, Hayato et al., "Tip-Sample Distance Control Using Photothermal Actuation of a Small Cantilever for High-Speed Atomic Force Microscopy", Review of Scientific Instruments, pp. 083702 1-6, 78, 083702 (2007), doi: 10.1063/1.2766825.

International Search Report mailed Sep. 10, 2013 in International Application No. PCT/GB2013/052256, filed Aug. 28, 2013.

Japanese Office Action dated Jun. 6, 2017 JP Application No. 2015-529119.

Akihiro Torii, "An AFM Encoder Using an Interferometer", Dengakuron C (The transactions of the Institute of Electrical Engineers of Japan C), vol. 122, No. 12, p. 2061-2066 (2002).

* cited by examiner

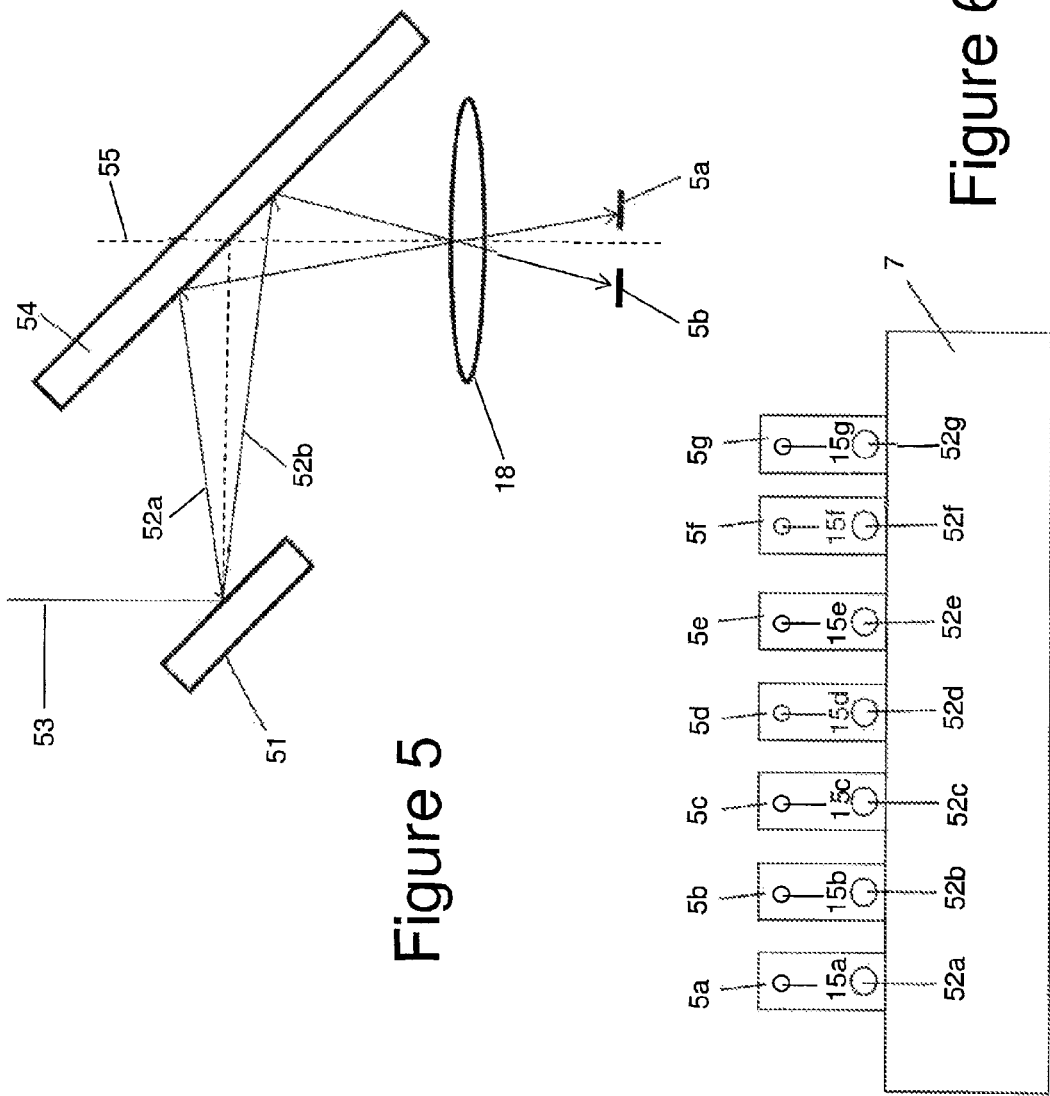

MULTIPLE PROBE DETECTION AND ACTUATION

FIELD OF THE INVENTION

The present invention relates to a method of detecting the positions of a plurality of probes, a method of actuating a plurality of probes, and apparatus operable to perform such methods.

BACKGROUND OF THE INVENTION

The speed of scanning in a probe microscope can be increased by operating two or more cantilevers in parallel, such that data is acquired simultaneously from each probe. Parallel operation in scanning probe microscopy (SPM) is a challenge because multiple probe detection must be implemented as well as independent actuation systems for each cantilever. As a result, parallel SPM systems have in the past differed significantly from conventional SPM systems. For example, some systems have deployed cantilevers with integrated piezo-resistive sensors, and integrated zinc oxide Z-actuators (Quate et al Applied Physics Letters vol. 67 No 26 3918 (1995)). A major difficulty with such integrated systems is the complexity and corresponding cost of the sensors. The designs are also inflexible since changing a simple parameter such as the pitch or spring constant of the cantilevers also requires a redesign of the layout and costly fabrication. As a result, parallel SPM systems of this sort have not been widely used. There is therefore a need for a parallel probe microscope that is flexible in operation and configuration. Furthermore, such a system should incorporate a probe detection system and a probe actuation system that have at least the performance of conventional SPM, while retaining compatibility with cantilever probes widely used in SPM.

Conventional probe microscopes employ piezo-electric elements to scan the cantilever or specimen with nanometer level accuracy or better. However, such piezo-elements often have a limited speed of response due to their size and mechanical characteristics. Smaller elements which can be integrated into the cantilever can be employed for fast scanning applications but the required fabrication and electrical connection is a challenge.

Photothermal actuation has therefore been developed, in which an infra-red laser is focused onto a cantilever and used to induce photothermal bending of the cantilever for both z-actuation and resonant excitation (Yamashita et al, Rev. Sci. Instrum. Vol 78, 083702 (2007). This approach is powerful and flexible, and can achieve a rapid response time due to the small size and short thermal time constant of the micromechanical cantilever. However this approach has not been used for parallel probe control due to the increased number of optical components needed for alignment and focusing.

Conventional scanning probe microscopes typically rely on optical lever detection for sensing cantilever motion but these systems are impractical to operate with multiple probes as the alignment is time consuming and difficult to automate. Interferometer based motion sensing, both homodyne and heterodyne, has also been used in SPM, but no systems have been reported for parallel probe sensing. This is likely to be due to the complexity, difficulty of alignment and corresponding increase in optical components that is required when scaling interferometer systems.

Microcantilever biosensors have been demonstrated as sensitive tools for chemical and biological detection on chip. Microcantilevers biosensors can be used in two different modes of operation: static and dynamic. In the static mode, the binding of target molecules to the cantilever is detected as a result of the surface stress and cantilever bending they cause. In the dynamic mode the cantilever is actuated and its resonant frequency is determined. The binding of the molecules is detected due to the mass change and resulting resonant frequency shift. Resonant cantilevers immersed in liquid suffer from high damping losses and reduced sensitivity.

One of the major difficulties of cantilever sensing in either mode is the measurement of cantilever displacement. The most common method for this measurement is the optical lever approach. A focused laser beam is reflected off the cantilever surface, and captured by a PSD (Position Sensitive Detector). The cantilever displacement causes movement of the laser spot on the PSD and a change in its output voltage. This method is very sensitive, but it requires elaborate free-space optics with precise alignment of the laser beam to the device under test. Moreover, the PSD signal's relationship to the cantilever's displacement depends on the exact position of the laser spot on the cantilever. This relationship is unimportant for resonant frequency measurements, but it greatly impacts static mode operation. For example, a change in PSD output due to slight laser misalignment can be misinterpreted as cantilever bending. Since the alignment cannot be perfectly reproduced, the laser must be kept aligned to the cantilever throughout the static mode experiment. This complicates parallel measurements. If a cantilever array is exposed to a sample, the response of only one device can be captured. Custom-made arrays of lasers and PSDs for measuring several cantilevers in parallel have been demonstrated. However, this approach leads to greatly increased instrumentation complexity and difficulty of alignment. It is not feasible to increase the number of lasers much further, while the number of cantilevers on a chip can easily be in the hundreds or even thousands.

Another common method for measuring cantilever response involves the integration of on-chip displacement sensors. This approach not only allows multiple devices to be measured in parallel, but also simplifies the external measurement setup. The built-in sensors can be piezoresistive, piezoelectric, capacitive, transistor-based, or optical. Unfortunately, all of these technologies greatly increase the fabrication complexity and cost of the cantilevers, which should be simple, cheap and disposable.

There is therefore a need for a parallel cantilever array readout instrument suitable for both static or dynamic operation which is reasonably cheap, capable of automated operation, and compatible with a wide variety of environments, from gases to complex fluid physiological systems.

SUMMARY OF THE INVENTION

A first aspect of the invention provides a method of detecting the positions of a plurality of probes, the method comprising: directing an input beam into an optical device; transforming the input beam with the optical device into a plurality of output beamlets (which optionally are not parallel with each other); splitting each output beamlet into a sensing beamlet and an associated reference beamlet; simultaneously directing each of the sensing beamlets onto an associated one of the probes (optionally with an objective lens) to generate a reflected beamlet; combining each reflected beamlet with its associated reference beamlet to generate an interferogram; and measuring each interferogram to determine the position of an associated one of the probes.

A second aspect of the invention provides a method of actuating a plurality of probes, the method comprising: directing an input beam into an optical device; transforming the input beam with the optical device into a plurality of actuation beamlets (which optionally are not parallel with each other); simultaneously directing each of the actuation beamlets onto an associated one of the probes (optionally with an objective lens), wherein each probe is arranged such that when the probe is illuminated by its respective actuation beamlet it deforms; and modulating the input beam over time in order to modulate the actuation beamlets and thus modulate the positions of the probes relative to the sample.

A third aspect of the invention provides a method of actuating a plurality of probes, the method comprising: directing an input beam into an optical device; transforming the input beam with the optical device into a plurality of actuation beamlets (which optionally are not parallel with each other); simultaneously directing each of the actuation beamlets onto an associated one of the probes (optionally with an objective lens), wherein each probe is arranged such that when the probe is illuminated by its respective actuation beamlet it deforms; and operating the optical device, or an optical element in a path of one or more of the actuation beamlets, with a control signal in order to modulate the intensity of one or more of the actuation beamlets over time and thus modulate the positions of one or more of the probes relative to the sample.

Further aspects of the invention provide apparatus arranged to perform the above methods as set out in the appended claims.

Thus a fourth aspect of the invention provides apparatus for detecting the positions of a plurality of probes, the apparatus comprising: an optical device arranged to transform an input beam into a plurality of output beamlets (which optionally are not parallel with each other); one or more beam splitters arranged to split each output beamlet into a sensing beamlet and an associated reference beamlet and simultaneously direct each of the sensing beamlets onto an associated one of the probes (optionally via an objective lens) to generate a reflected beamlet; and one or more sensors arranged to measure inteferograms which are generated by combining each reflected beamlet with its associated reference beamlet to determine the positions of the probes.

A fifth aspect of the invention provides apparatus for actuating a plurality of probes, the apparatus comprising: an optical device arranged to transform an input beam into a plurality of actuation beamlets (which optionally are not parallel with each other) and simultaneously direct each of the actuation beamlets onto an associated one of the probes (optionally via an objective lens), wherein each probe is arranged such that when the probe is illuminated (and optionally heated) by its respective actuation beamlet it deforms to move the probe (optionally towards or away from a sample); and a controller arranged to modulate the input beam over time in order to modulate the actuation beamlets and thus modulate the positions of the probes relative to the sample.

A sixth aspect of the invention provides apparatus for actuating a plurality of probes, the apparatus comprising: an optical device arranged to transform an input beam into a plurality of actuation beamlets (which optionally are not parallel with each other) and simultaneously direct each of the actuation beamlets onto an associated one of the probes (optionally via an objective lens), wherein each probe is arranged such that when the probe is illuminated (and optionally heated) by its respective actuation beamlet it deforms to move the probe (optionally towards or away from a sample); and a controller arranged to operate the optical device, or an optical element in a path of one or more of the actuation beamlets, with a control signal in order to modulate the intensity of one or more of the actuation beamlets over time and thus modulate the positions of one or more of the probes relative to the sample.

Instead of using multiple input beams, each generated by a respective laser, a single input beam is transformed into multiple beamlets which are then directed onto the probes for the purpose of position detection (in the first and fourth aspect of the invention) or actuation (in the second, third, fifth and sixth aspects).

Where the beamlets are used for actuation, then the input beam can be modulated over time (either with a regular period or aperiodically) in order to modulate the actuation beamlets and thus modulate the positions of the probes relative to the sample. Independent actuation for each probe is not necessarily required in all modes of operation. However, where independent actuation of the probes is required then the method may further comprise modulating a selected frequency range of the input beam over time in order to modulate a frequency range of the actuation beamlets and thus modulate the position of a selected probe (or probes) relative to the sample independently of the other probes, wherein the selected probe(s) has a resonant frequency which is different from a resonant frequency of the other probes and which matches the selected frequency range. This provides a method of independently actuating the probes at a high modulation rate if such a high modulation rate is not possible with the optical device, although it is only suitable for varying a periodic resonant motion.

An objective lens may be arranged to simultaneously direct each of the actuation and/or sensing beamlets onto an associated one of the probes. Where such an objective lens is provided then the actuation and/or sensing beamlets are typically not parallel with each other as they enter the objective lens.

Each probe is typically arranged such that when the probe is illuminated by its respective actuation beamlet it deforms to move the probe relative to the sample—typically towards or away from the sample.

The deformation of the probe may be a flexural deformation, a torsional deformation, or any other deformation. The deformation may be static or dynamic.

Preferably each actuation beamlet causes its respective probe to heat and deform by the photothermal effect. The term "photothermal effect" is used herein to refer in general terms to the deformation of the probe caused by the heating of the probe, such heating of the probe being induced by its illumination. Alternatively the actuation beamlets may cause them to deform by some other mechanism such as by radiation pressure. Radiation pressure can be used in combination with highly reflective probe coatings and ideally some form of cavity, possibly a mirror attached to the probe.

Each probe may comprise two or more materials with different thermal expansion coefficients which are arranged such that when the probe is heated by its respective actuation beamlet it deforms to move the probe relative to a sample. Alternatively each probe may be made of a single material—in this case it will deform due to a thermal gradient introduced by heating a region of the probe and thus inducing mechanical stress, typically between a side of the probe which is heated by the actuation beamlet and the opposite side of the probe.

Typically each reflected beamlet and its associated reference beamlet are directed onto a sensor with a sensor lens, and the sensor measures each interferogram to determine the position of an associated one of the probes.

The optical device may be a passive device which cannot modulate the intensity or angle of the beamlets over time. Alternatively it may be operated with a control signal (typically an electrical signal) in order to modulate the intensity (power) of one or more of the actuation beamlets over time (either with a regular period or aperiodically) and thus modulate the positions of one or more of the probes relative to the sample. All of the probes may be moved in unison in this way, for instance to move them in unison to a sensing position. Alternatively the positions of one or more of the probes may be modulated by the optical device relative to the sample independently of other ones of the probes, for instance in order to independently control each probe's separation from the sample for imaging purposes, or to move one or more of the probes into an imaging position whilst leaving the rest of the probes in an inactive position in which they do not interact with the sample.

The optical device may be operated with a control signal in order to modulate an angle of one or more of the beamlets over time relative to the optical axis of the objective lens. Again the angles of all beamlets may be modulated in unison, for instance in order to track a scanning array of probes, or the optical device may be operated in order to independently modulate the angle of one or more of the beamlets over time relative to other ones of the beamlets output by the optical device.

The optical device typically transforms the input beam by diffraction, although as an alternative it may transform the input beam by reflection, for example, using an array of microelectromechanical systems (MEMS) mirrors.

The optical device typically imposes a spatially varying phase and/or amplitude modulation on the input beam.

The optical device may comprise a diffractive optical element (DOE). Preferably the optical device comprises a spatial light modulator (SLM) such as a liquid crystal SLM.

Typically the plurality of probes comprises ten or more probes. Optionally the plurality of probes may comprise one hundred or more probes.

The probes may be arranged in a single straight line, or in a two-dimensional array.

The probes may be used in a number of applications, including (but not limited to): scanning probe microscopy, for example for extreme ultraviolet (EUV) mask inspection and review; biosensing to detect multiple biomarkers; nanolithography, such as dip pen nanolithography in which scanning probes deposit chemical compounds on a substrate; or data storage in which each probe has a heater allowing its temperature to be independently raised to melt a polymer substrate followed by an imprinting action by the probe producing a dent representing a binary digit.

BRIEF DESCRIPTION OF THE DRAWINGS

Embodiments of the invention will now be described with reference to the accompanying drawings, in which:

FIG. 5 illustrates the actuation system in detail;

FIG. 6 shows a linear array of seven probes and the illumination spots created by their associated sensing and actuation beamlets;

DETAILED DESCRIPTION OF EMBODIMENT(S)

Figure 1:
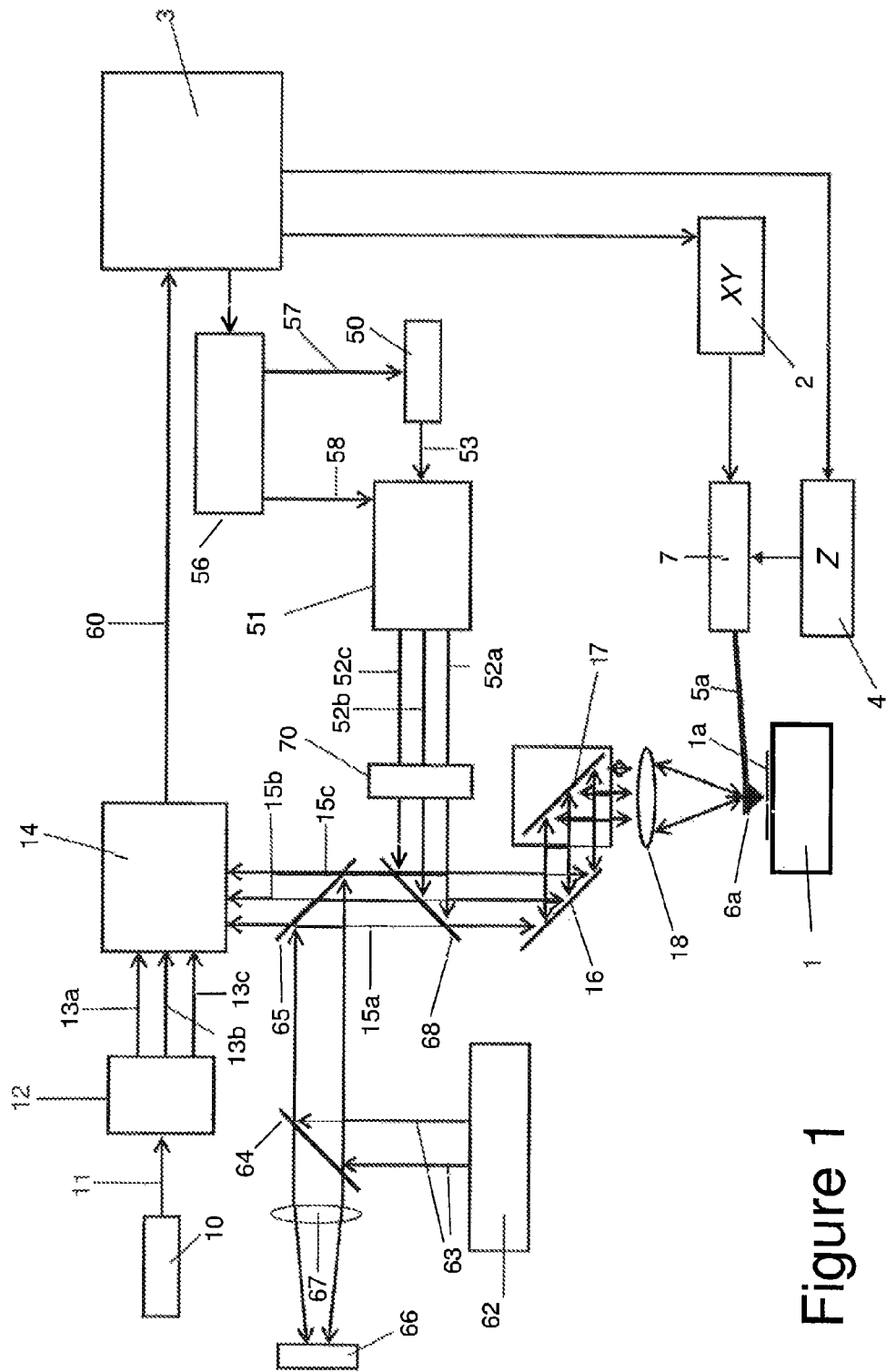
FIG. 1 is a schematic drawing of a scanning probe microscope.

With reference to FIG. 1, a scanning probe microscope that incorporates an interferometer based sensing system and photothermal actuation system in accordance with the present invention is shown. The microscope comprises a moveable stage 1 adapted to receive a sample 1a whose surface is to be investigated by an array of thermal actuated bimorph probes, only one of which is shown in FIG. 1. The scanning capability is provided by two conventional drive systems: an x,y scanner 2 operable by an SPM controller 3 to provide relative motion of the probe array in the plane (x, y) of the sample 1a; and a z positioning system comprising piezoelectric drivers 4 operable to move the probe and sample towards and away from each other (z direction) over ranges larger than that achievable by the photothermal actuation of the probe array.

The probe array comprises a linear array of cantilever beams 5a, each carrying a tip 6a which tapers to a point, and which is located towards a distal end of the cantilever beam. The other (base or proximal) end of each cantilever beam 5a is supported by a mount 7. In this embodiment, the z-positioning system 4 is connected to the probe mount 7. Alternatively, it may be connected to the sample stage 1.

The probe tip 6a comprises a three dimensional, often conical or pyramidal structure that is located at the free end of each cantilever beam 5a. The tip tapers to a point that is its closest point of interaction with a surface under interrogation. The cantilever is the beam itself, excluding the tip, that supports the tip at one end and at the other is held by the microscope apparatus. The cantilever 5a and tip 6a together are referred to as the probe.

Each probe is generally fabricated from silicon or silicon nitride. Typically, the cantilever 5a is around 50-200 µm long, 20-50 µm wide and around 0.2-2 µm thick, but this size can of course be varied according to application. The shape may also be varied: typically it is rectangular or triangular with, in the latter case, the tip in the vicinity of its apex. The tip is typically 5 µm at its base, 3~10 µm high and with an end radius of curvature of 2-20 nm. In use, the fine point at the end of the tip 6a is oriented towards the sample 1a. Recently, smaller dimension probes have been fabricated for use at faster imaging speeds. These probes have cantilevers around 520 µm long and 3-10 µm wide, with a correspondingly smaller tip. The tip may be formed as part of the cantilever beam fabrication process or added as a post processing step, for example, using electron beam deposition (EBD) to create a diamond like carbon (DLC) spike. Additionally, the cantilever beam is coated in a metal, typically, gold or aluminum, to increase the reflectivity of the cantilever beam when using an optical method to detection method.

The system is in principle capable of any conventional SPM imaging mode, and also more advanced modes developed for industrial inspection, such as, the inspection of semiconductor wafers or photo-masks. The system uses SLM units to create, steer and modulate multiple beams within the interferometer sensing system and the photothermal actuation system, thereby allowing parallel operation of an array of cantilever probes.

Figure 2:
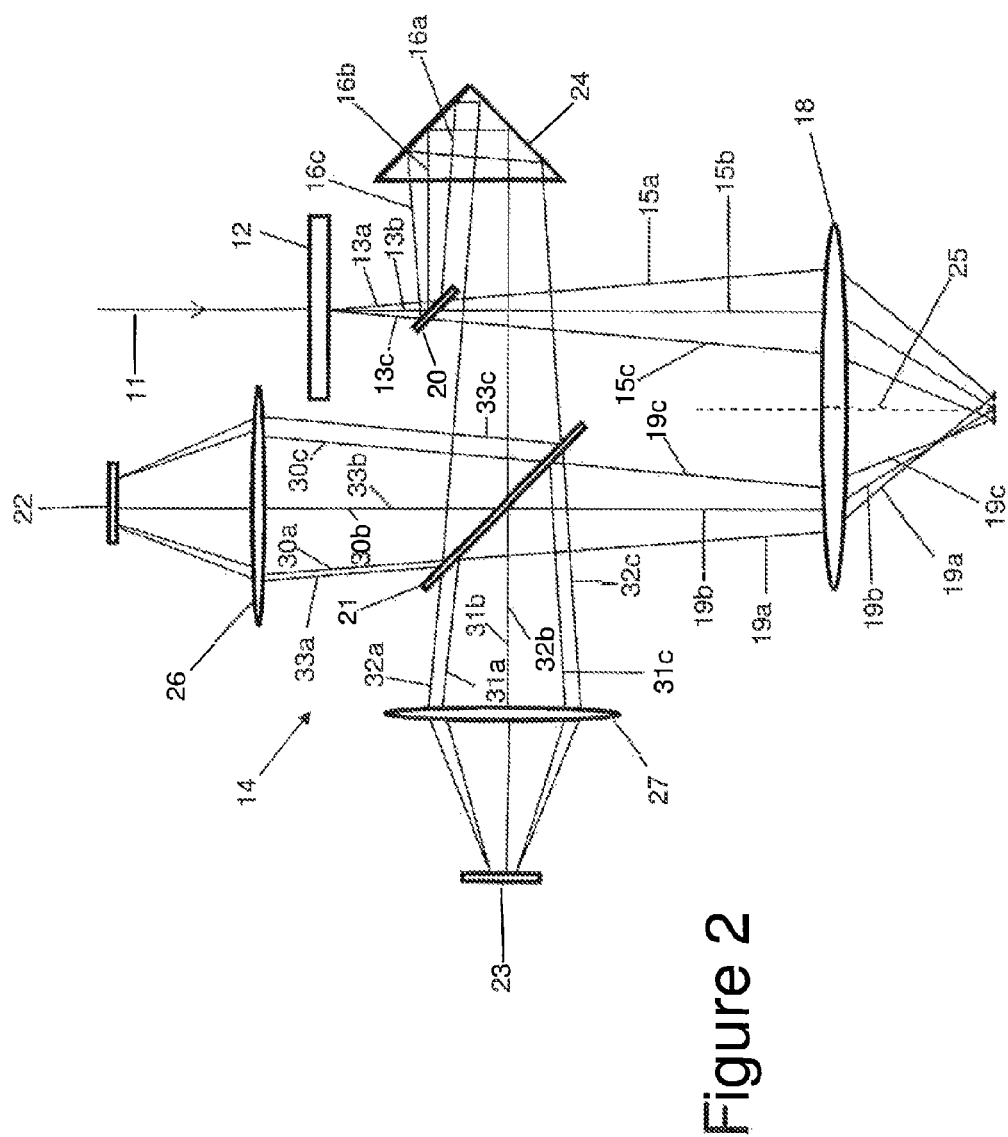
FIG. 2 illustrates the interferometer in detail.

With reference to both FIGS. 1 and 2, a detection laser 10 generates a detection input beam 11 which is incident on a Spatial Light Modulator (SLM) 12 where the beam is split into the required number of beamlets 13a-c. Typically the beam 11 is split into one beamlet 13a-c for every cantilever in the array. Alternatively the beam 11 may be split into two or more beamlets 13a-c per cantilever to measure heights or relative heights at different locations (for example one at the tip and another at the base to measure bending of the cantilever).

It would be practically difficult and complex to implement passive optical elements for this purpose, and so the SLM 12 is employed for the flexibility and ease of integration into an optical system while allowing computer control for rapid alignment. A brief description of the principles of the SLM 12 follows. Suitable SLMs are supplied by Boulder Nonlinear Systems, Colorado, USA such as their XY Series products and Hamamatsu such as their X10468 Series products.

In an exemplary SLM, in order to modulate the phase of incident light, a nematic liquid crystal SLM is aligned in a planar conformation. Here the liquid crystal director (i.e. long axis of the molecules) is oriented parallel to the polarization of the incident light. Upon application of a voltage, the molecules tilt in a direction parallel with the direction of propagation of the optical field. This causes the incident light to encounter a reduced refractive index. The change in refractive index translates directly to a change in the optical path, and consequently a phase shift for the incident light. If enough voltage is applied, the variation in refractive index ranges from the extraordinary index (for no applied voltage) to the ordinary index (maximum tilt of the molecules). A typical change in the refractive index for maximum applied voltage is 0.2. In the preferred embodiment the SLM 12 uses very large scale integration (VLSI) to address an array of liquid crystal modulators. The VLSI addressing allows for multiplexing to achieve individually addressable pixels across the entire optical aperture. This flexibility results in a randomly addressable phase mask that acts as an optical phased array with the potential for phase correction. The SLM optical head itself consists of a layer of liquid crystal sandwiched between a cover glass and a VLSI backplane.

The beamlets 13a-c then enter an interferometer 14, shown in detail in FIG. 2, where they are split by a beam splitter 20 into sensing beamlets 15a-c and reference beamlets 16a-c. The beam splitter 20 may create a lateral shift of the beam but no angular deviation.

The sensing beamlets 15a-c leave the interferometer and are reflected by a fixed mirror 16 onto a tracking mirror 17 (shown in FIG. 1 but omitted from FIG. 2) that steers the beamlets during XY scanning so that they remain optimally positioned on the cantilevers. The tracking mirror 17 comprises a scanning mirror which reflects the beamlets 15a-c at an angle which varies synchronously with the x,y scanner 2. Alternatively the tracking mirror 17 may be omitted and this steering function undertaken by the SLM 12, depending on the speed requirements. The sensing beamlets 15a-c, having been steered by the tracking mirror 17 or SLM 12, are then focused by an objective lens 18 onto the ends of the cantilevers where they are reflected back towards the objective lens 18. The lens 18 collects and collimates the reflected beamlets 19a-c and projects them back into the interferometer 14, where they are split into two components 30a-c and 31a-c by a phase shifting beam splitter 21 and incident on photodiodes 22,23. The reference beamlets 16a-c are each split by the phase shitting beamsplitter 21 into two components 32a-c and 33a-c and incident on the photodiodes 22,23 where they are interfered with their associated reference beamlets 30a-c and 31a-c. The coating of the phase shifting beam splitter generates a phase quadrature relationship between the pair of interferogram beams produced by the overlapping reference beamlets 32a-c and 33a-c and associated reference beamlets 30a-c and 31a-c.

Although the lens 18 is illustrated as a single lens element, it will be understood that it may comprise an assembly of multiple lens elements.

After signal processing the signals are sent from the interferometer 14 to the SPM controller 3, which is adapted for parallel operation, each data channel representing the position of a point on a cantilever within the array with respect to a reference point.

The reference beamlets 16a-c are directed towards a suitably positioned retro-reflector 24, and thereafter to the beam splitter 21, where the reference beamlets are split and recombined with the two sensing beamlet components to create first and second interferograms with a relative phase shift of 90 degrees. The interferograms are detected respectively by the first and second photodiodes 22,23. Interferometric methods of extracting the path difference between two coherent beams in such a homodyne interferometer are well known in the art and so will not be described here.

The two interferograms should ideally produce signals from the photodiodes which are complementary sine and cosine signals with a phase difference of 90 degrees. The signals should have equal amplitudes with no DC offset and only depend on the displacement of the cantilever and wavelength of the laser. Due to practical limitations, such as imperfect optical components and alignment, the signals are typically not perfectly harmonic, with equal amplitude, in phase quadrature and without a DC offset. Thus known methods can be used to monitor the photodiode output signals while changing the optical path length difference in order to determine and to apply corrections for these errors.

The phase quadrature signals from the photodiodes are suitable for use with conventional interferometer reversible fringe counting and fringe subdividing techniques which, for example, may be implemented using dedicated hardware, programmable hardware such as an FPGA or as a programmed computer. Methods for subdividing or interpolating based on the are tangent of the quadrature signals are well known and can provide sub nanometer resolution.

Note that optionally the retro-reflector 24 may be replaced by a lens and a planar mirror. This might be advantageous in a non-infinity-corrected system where the probes are not at the focal plane of the objective lens 18.

The beamlets 13a-c are steered by the SLM 12 so that the sensing beamlets 15a-c propagate at different angles relative to the optical axis 25 of the objective lens 18, such that when they reach the objective lens 18 it focuses each beamlet at the required place on the back of each cantilever in the array, in the focal plane of the lens for an infinity-corrected system. The SLM 12 achieves this diffractive beam steering with an optical phased array analogous to a radar system. Note that the angular deviations of the beamlets from the axes of the interferometer are only a few degrees at most, hence they are exaggerated in FIG. 2. The separation of the beamlets by the objective lens 18 onto the cantilever array has correspondingly been greatly exaggerated so that they can be visualized. Each beamlet is then reflected back off the cantilever and collected by the objective lens 18. The beamlet is then collimated by the objective and propagates back towards the beam splitter 21, retaining however the same magnitude of angular orientation with respect to the optic axis of the system. Meanwhile each reference beamlet has passed through the retroreflector 24 and beam splitter 21 and the matching reference beamlets are overlapped with the sensing beamlets as they propagate towards lenses 26,27 in front of multi-segment photodiodes 22 and 23. These lenses 26,27 focus the collimated beamlets down to a series of spots on the multi-segment photodiodes 22,23, each corresponding to a cantilever in the array. The position of each spot is directly related to the angular deviation of the beam from the optical axis, and hence the reference and sensing beamlets recombine to produce an intensity signal that can be related to the optical path length between them. In this way, parallel interferometric position sensing of each cantilever in the array can be achieved with sub-nanometer resolution and high bandwidth. The interferometer described herein is one example of a homodyne system. The particular system described offers a number of advantages to this application. The use of two phase quadrature interferograms enables the measurement of cantilever displacement over multiple fringes, and hence over a large displacement range. The use of a phase-shifting coating on the beamsplitter 106 used to generate the pair of phase quadrature interferograms reduces the interferometer's sensitivity to polarisation effects, for example arising from changes in polarisation as the light beam is reflected from the cantilever. Examples of an interferometer based on these principles are described in U.S. Pat. No. 6,678,056 and WO2010/067129. Alternative interferometer systems capable of measuring a change in optical path length may also be employed with this invention, for example, a homodyne interferometer could be implemented using polarization methods to generate the two phase quadrature interferograms or a heterodyne interferometer implemented by using a dual frequency laser A suitable homodyne polarisation based interferometer is described in EP 1 892 727 and a suitable heterodyne interferometer is described in U.S. Pat. No. 5,144,150 which could be adapted for use with this invention.

The position of the probe will affect the path of the reflected beamlets 19*a-c* and position of their associated spots on the photodiode 22,23. Although the angle of the probe will affect the reflected angle of the beamlet it is the height and position of the probe in the focal plane of the objective lens 18 which is particularly critical. In theory, light propagating from any angle from a single point in the focal plane of the objective lens 18 will arrive at a single point on the photodiode 22,23. This is because the focusing lens 26,27 in front of the photodiode is forming an image of the object, i.e. probe array, placed in the focal plane of the objective lens 18. One way to visualise this is to consider that light propagating from any angle from a single point in the focal plane of the objective lens 18 will produce a collimated beam of light after the objective lens which will be focused to a single point by the photodiode focusing lens 26,27. Note, this is for an infinity corrected optical system where the probe and photodiodes 22,23 are in the focal plane of the objective lens 18 and focusing lens 26,27 respectively.

Now considering a change in height of the probe, this will affect the formation of the spot on the photodiode. In fact, it will not only affect the position of the spot but also the shape of the spot, i.e. it will be out of focus. This will affect the ability to create an interferogram with the reference beam. This can be visualised by the reflected beam of light after the objective being slightly converging or diverging and thus the wave front of the beam will be distorted compared to the reference beam which will affect the contrast of the interferometer.

Figure 3:
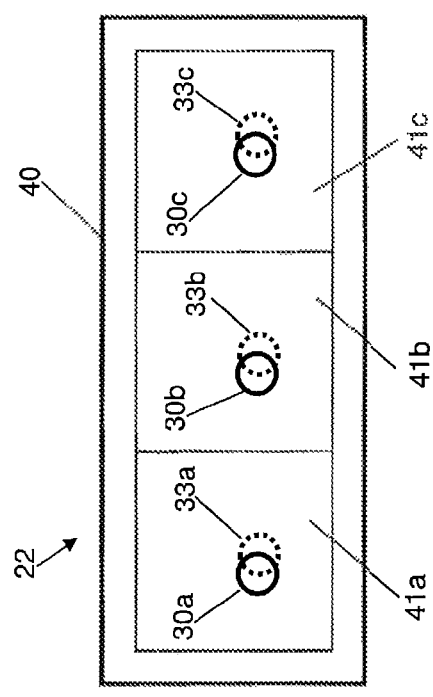
FIGS. 3 and 4 show two alternative photodiode arrays.

However it is not necessary for the sensing beamlets and reference beamlets to completely overlap on the photodiode 22,23. FIG. 3 shows part of the photodiode 22, along with the overlapping spots associated with the sensing beamlets 30*a-c* and reference beamlets 33*a-c*. The region where the beams overlap will form an interferogram and the larger the overlap the greater the intensity change of the constructive and destructive interference associated with a path length change between the sensing and reference beamlets. The regions which do not overlap simply form a DC offset on the intensity measured by the photodiode. If the degree of overlap between the spots changes, the magnitude of the intensity variation due to the interference will change, but the average DC offset measured will remain the same. Obviously it is preferred to maximise the overlap of the spots and thus signal to noise ratio, however, variations in the overlap can be accommodated.

The photodiode 22 has a body 40 and three photosensitive regions 41*a-c*. The optical system is configured such as to direct each overlapping pair of beamlets onto the centre of a respective one of the photosensitive regions 41*a-c*, so that the output of each region 41*a-c* represents the true instantaneous height of an associated one of the probes in the z direction. This is independent of the position of the base of the probe relative to the tip i.e. of the deflection.

In the case of FIG. 3 the intensity of each interferogram is monitored independently as each interferogram is located on a separate region 41*a-c* of the photodiode 22. The pitch and position of the interferograms is controlled by the magnification of the optical system which is determined by the focal length of the photodiode lens 26,27 divided by the focal length of the objective lens 18.

Figure 4:
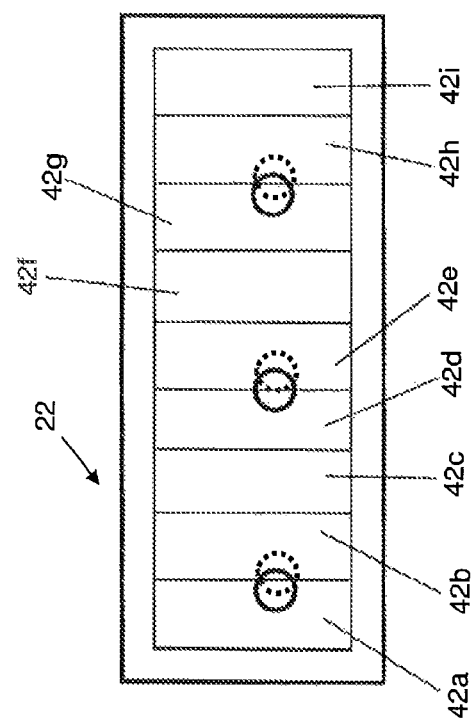

Optionally a greater number of photodiode regions than interferograms can be used as shown in FIG. 4 in which the photodiode 22 has nine regions 42*a-i* and the regions over which each interferogram falls can be summed to determine the interferogram's intensity. This allows for adjustments in pitch of the interferograms which may be required to accommodate changes in probe pitch.

Note that it is possible to use a 2D photodiode array if a 2D array of probes and thus interferograms is to be measured.

Returning to FIG. 1, the microscope has a photothermal actuation system for bending the probes which will now be described. Light from an IR laser 50 is incident on a second SLM 51, where it is split into actuation beamlets 52*a-c*, at least one per cantilever in the array. The beamlets 52*a-c* are then reflected by a dichroic mirror 68 and the tracking mirror 17 (shared with the interferometer 14) which maintains them in position on the cantilevers as they are scanned in XY. The beamlets 52*a-c* are then focused by the objective lens 18 onto the cantilevers and precise positioning is achieved by steering the beamlets using the SLM 51. The photothermal actuation system is capable of controlling the cantilevers in a number of ways, with great flexibility and control. For example, by steering each beamlet to the base of the cantilevers, the photothermal effect can be used to deflect the cantilever up and down for the purposes of cantilever selection, or alternatively, z-actuation in the case of conventional SPM feedback control. If the cantilevers are required to resonate, which is a common requirement for a number of SPM imaging modes, the IR laser 50 can be modulated to drive the cantilevers at one or more of the resonant frequencies. Furthermore different cantilevers can be designed and fabricated differently to resonate at different frequencies to allow completely independent operation. The above examples of operating modes are not intended to be restrictive in any way but do give some example of the range of capabilities of the parallel probe SPM.

With reference to FIG. 5, a more detailed illustration of the parallel probe photothermal actuation system is shown. Light 53 from the laser source 50 is expanded into a parallel beam and directed to be incident on the SLM 51 so as to fill the aperture of the SLM 51. The diagram illustrates a 45 degree angle of incidence at the SLM 51 although other angles could be employed for greater efficiency. Only one ray from each beamlet 52a and 52b is shown to illustrate the beam paths in order to simplify the diagram. When the SLM 51 is switched off, the incident light is specularly reflected off the SLM 51 and directed towards the back of the objective lens via a beam splitter 54, following the path of a dotted line 55 along the optic axis of the objective lens 18. Only two cantilevers 5a and 5b are illustrated in this diagram, for simplicity. In order to illuminate the two cantilevers, it is necessary to split the beam. This is achieved by the SLM 51, which is programmed to steer each beamlet 52a,b towards the back of the objective lens 18, close to the optical axis 55, so that the objective lens focuses the beamlets 52a,b at the required place on the back of each cantilever 5a,b in the focal plane of the objective lens. This is illustrated by two ray paths that pass through the optical centre of the objective lens 18. The angles of the rays with respect to the optical axis are greatly exaggerated for illustration purposes. The SLM 51 operates in a similar fashion to the SLM 12, although the SLM 51 reflects the input beam whereas the SLM 12 transmits it. Like the SLM 21, the SLM 51 achieves diffractive beam-steering with an optical phased array analogous to a radar system. The diffractive optical phased array can be thought of as a quantized multiple level phase grating. The more phase levels used in the array, the higher the diffraction efficiency. For example, a binary phase grating ideally provides a diffraction efficiency of 40.5% in each of the two first order diffracted beams.

FIG. 6 is a view showing a linear array of seven cantilevers 5a-g each illuminated by a respective actuation beamlet 52a-52g at its proximal end near the mount 7 and by a respective sensing beamlet 15a-g at its distal end above the tip 6a (which is on the opposite side of the cantilever and hence not shown in FIG. 6). With a suitable objective lens 18 it is possible to achieve a spot size for the actuation beamlets 52a-52g and sensing beamlets 15a-g of only a few microns, allowing the precise application of infra-red radiation to a specific location on the cantilever as required for efficient photothermal actuation. Using the SLM it is also possible to control the size of the focused spot produced by each beamlet as shown in FIG. 6 in which the actuation beamlets 52a-52g create spots which are larger than those created by the sensing beamlets 15a-g.

The cantilevers 5a-g are thermal bimorph structures, the materials of which undergo differential expansion when heated. That is, they are composed of two (or more) materials, with differing thermal expansions. Typically, this will be a silicon or silicon nitride base with a gold or aluminium coating. The coating extends the length of the cantilever and covers the reverse side from the tip. The actuation light source 50 preferably emits light 53 of one or more wavelengths at which there is a maximum or peak in the absorption spectrum for the particular coating. For example the wavelength may be around the aluminium absorption peak at ~810 nm. Other coating/wavelength combinations can be used, for example gold has a higher absorption below 500 nm light. When this light is incident on the coating side of the cantilevers, the aluminium expands to a greater degree than the silicon nitride, bending the cantilever such that the tip moves downwards, towards the sample. If illumination intensity is increased, the tip therefore moves closer to the sample surface. Conversely, if the intensity is lowered, bending is decreased and the tips are moved away from the sample. Other arrangements of coating and base materials may result in bending in an opposite direction in response to illumination.

The cantilevers 5a-g are shown with a constant spacing (pitch) between them, but optionally the spacing between adjacent cantilevers may vary across the width of the array. The SLM 12 can be controlled to adapt to a probe array with such a varying pitch. Referring to FIG. 1: the actuation light source 50 is controlled by a signal generator 56 that, in turn, is linked to the SPM controller 3. The signal generator 56 is operable to control the intensity of the light 53 emitted from the actuation light source 50 and thus controls the intensity of the beamlets 52a-c in unison at a high modulation rate of typically 100's of kHz to 10's of MHz. The SLM 51 on the other hand can independently control the intensities of individual ones of the beamlets 52a-c, although at a lower rate typically 100's of Hz but no higher than 1 kHz. The intensity of the beamlets 52a-c determines the degree of bend exhibited by the thermal bimorph probes (regardless of their material specifics) and so governs the tip—sample separation distance during the course of a scan.

The intensity of light 53 emitted from the actuation light source 50 is modulated as the scan progresses in accordance with parameters that will be described in the next section. Essentially, the actuation light source 50 and SLM 51 can be considered to provide the drive mechanism for both the z position feedback and the probe oscillation. That is, they are set to drive oscillation of each cantilever probe and to adjust each probe—sample separation distance during the course of a scan. In an alternative embodiment, instead of modulating the intensity of the light 53 emitted from the light source or modulating the intensity of the individual beamlets 52a-c by operation of the SLM 51, the intensity of the individual beamlets 52a-c can be modulated by an optical element 70 such as an acousto-optic modulator (AOM) or electro-optic modulator (EOM) in the path of the beamlet between the SLM 51 and the probes.

Specific embodiments of the imaging modes of the SPM will now be described in more detail.

The parallel probe microscope is especially suitable for examining large, substantially flat, surface areas to detect features on the nanometer scale, at the high speeds required for effective industrial application. A prime example of such an application is the inspection of Extreme Ultra-Violet (EUV) masks. A critical issue to be addressed for commercialization of EUV lithography is the detection and reduction of defects on the masks and in particular on blank mask. Typical defects on blank masks are either pits or particles which can originate either on the substrate, during multilayer deposition or on top of the multilayer stack. The buried defects are especially problematic, and 10 nm defects and small may be considered an issue. For example, the phase shift caused by a 3 nm variation in mask substrate flatness is sufficient to produce a printable defect. SPM is in principle well suited to the detection of such defects, but single probe instruments are too slow for industrial applications. A parallel probe instrument of typically ten probes or more is required to achieve acceptable scan speeds. The exemplary operating mode of such an instrument, which is based on a cyclic oscillation of each probe, is described in the following section.

In taking an image of the sample, the SPM is operated as follows. The signal generator 56 provides a source signal 57 that oscillates at the desired frequency and amplitude. This signal 57, on input to the actuation IR light source 50, causes each of the beamlets 52a-c emitted by the SLM to modulate its intensity in relationship to the waveform of the signal.

When this modulated light is incident on each cantilever, it causes a flexing of the cantilever that varies with the intensity modulation. The probe tip is therefore driven towards and away from the sample at a frequency and amplitude that, in free space, is the same as that of the drive signal 57. The probe oscillation frequency is normally chosen to be at or near resonance. Alternatively, the probe can be driven off-resonance but still at a high frequency. It is important to note that each probe can be driven at resonance by a single drive signal 57 (without being further modulated by the SLM 51) as the probes can be fabricated so as to have substantially the same resonant frequency. The SLM 51, which has a limited speed of response, can be used to independently modulate the overall amplitude of each beamlet 52a-c as well as its angle (and hence its position on the cantilever) in accordance with a second drive signal 58 as required in the operating mode described below. Alternatively, each probe can be fabricated to have a somewhat different resonant frequency by suitable design, for example by changing a dimension such as the width of the cantilever. In this case the drive signal 57 causes the IR laser 50 to generate an input beam 53 which contains multiple frequency components that each correspond to the resonance of a selected probe (or group of probes). The amplitude of oscillation of each probe may then be adjusted by varying the amplitude of the relevant signal frequency component via the signal 57. In this case, the control signal 58 only causes the SLM 51 to control the positions and relative intensities of the beamlets 52a-c.

In operation, each cantilever probe is simultaneously irradiated by a respective modulated-intensity beamlet 52a-c, as described above, such that it oscillates with the desired free space amplitude. The probe mount 7 is then moved towards the sample using the z-actuator 4, so that all the probes are within a specified range of the surface. This is relatively straightforward if the surface is substantially flat. After initial z positioning of the probe mount 7, there will be some variation in the height of each probe above the surface. This can be compensated for by mechanically tilting the mount 7 until all probes are at the same height above the surface. Alternatively it can be compensated for by irradiating the probes with the laser 50 and using the SLM 51 to independently modulate the amplitude of each beamlet 52a-c in accordance with the second drive signal 58 so that individual probes (or groups of probes) bend towards the surface and stop when they are within range. Alternatively it can be compensated for by a combination of the above.

Furthermore, it may be desirable to only have a subset of the probes at an imaging position at a set height above the surface. For example with an array of ten probes it may be desirable to only have five probes (for example every other probe) at an imaging position at any one time. Then if one of the five probes becomes damaged, the five probes can be retracted from the sample 1a and the other five probes moved into position. Such slow gross probe z positioning can be achieved by the SLM 51 and control signal 58 which can operate to select or retract individual probes (or groups of probes) from the imaging position independently of the other probes in the array.

The signal generator 56 then increases the signal 57 to the actuation light source 50 so that the probe tips begin to engage in intermittent contact with the surface. The nature of an oscillating probe in intermittent contact with a surface are complex, and will depend on many factors including probe design, tip geometry and chemistry as well as surface topography and chemistry. However in broad terms the oscillation amplitude of each probe is reduced as the tip moves towards, and begins to interact with, the surface, such that the lowest point of the tip oscillation corresponds to the point at which the tip is in contact with the sample surface. In this way each probe effectively samples the surface at a frequency determined by the actuation laser drive frequency.

The oscillation amplitude is controlled so that the forces on each tip are maintained within set levels to ensure no damage occurs to the tip or surface. Such amplitude control can be achieved in a number of ways. Firstly, the z-positioning system 4 can be operated to move the probe mount 7 and move the probes towards or away from the sample in unison. Secondly, the drive signal 57 can cause the IR laser 50 to generate an input beam 53 which varies in amplitude and hence the amplitude of motion of the probes is changed in unison. Thirdly, the SLM 51 and control signal 58 can operate to slowly change the amplitude of motion of individual probes (or groups of probes) independently of the other probes in the array. Fourthly, each probe can be fabricated to have a somewhat different resonant frequency by suitable design, for example by changing a dimension such as the width of the cantilever. In this case the drive signal 57 causes the IR laser 50 to generate an input beam 53 which contains multiple frequency components that each correspond to the resonance of a selected probe (or group of probes). The amplitude of oscillation of each probe (or group of probes) can then be adjusted quickly and independently of the other probes by varying the amplitude of the relevant signal frequency component via the signal 57.

Each probe is continually monitored throughout its oscillation by the parallel interferometric detection system 14, which outputs a signal 60 for each probe that corresponds to the instantaneous position of the probe at a given point in time. Considerable amounts of data are generated in this way for a high speed scanning system. The SPM controller 3 therefore incorporates a field programmable gate array (FPGA) which is configured in order to provide the necessary processing capability. As is known in the art, alternative signal processing techniques such as digital signal processing (DSP) or a dedicated analogue or digital electronic method may be used. The probe cyclic motion typically has a frequency range of 10's to 100's of kHz and sampling frequency for data recording is in the region of 100 MHz. Consequently, each cycle of probe movement is sampled in the region of 1000 to 10,000 times, which is more than sufficient to analyse the height detector signal 60 to obtain a surface height detection point for each tip in the array. There are a number of ways that the instantaneous height detection signal can be processed to derive a surface height reading for any given probe. However in the simplest case readings can be based on the lowest recorded point in the probe oscillation cycle, when the probe tip is considered to be substantially in contact (or close to contact) with the surface.

The xy scanner 2 translates the cantilever array across the surface of the sample in order to generate an image of the surface. The controller 3 ensures that the tracking system 17 is matched with the scan pattern driven by the scanner 2 such that light from both the IR actuation source 50 and the detection source 10 maintain their position on each probe (shown in FIG. 6) in the array as it moves. The controller 3 may calculate different drive signals for the scanner 2 and tracking system 17 depending on their particular construction and mechanical behaviour. If the sample is scanned the tracking system may not be required if the sample is moved such that the probe, detection and actuation system remain in a fixed registration.

In this way the probe array is scanned over the surface, with the microscope collecting data from each probe within the array to provide a spatial map of the surface, formed of data points with sub-nanometer vertical and horizontal resolution. It will be appreciated that many scan operating patterns can be followed to collect data, depending on the kind of inspection information required. In the case of investigating defects on EUV masks, a large surface area must be inspected due to the low levels of defects. Typically the scan pattern will follow a raster pattern, with ten parallel probes providing a data acquisition rate increase of about ten times compared with the case of a single probe microscope.

It will be appreciated that as the array is translated in the XY plane, each probe tip will encounter a different surface segment at the low point of each probe oscillation cycle as it engages with the surface. As the surface is not completely smooth, the tip will therefore engage at different points in the oscillation cycle and the surface height of a given segment extracted as described above. No adjustments are made to the cantilever base height on a segment by segment basis, as in conventional SPM where a feedback loop operates. However for substantially flat samples scanning the array at a constant separation with the sample and not making any adjustments may be acceptable, and confer significant advantages. For example, it should be emphasized that the scan speed of the parallel probe microscope is not limited by the z-actuation feedback loop when operated in this mode, as is the case with a conventional SPM. The parallel probe microscope is capable of operating at scanning speeds considerably in excess of the limit imposed by feedback on reasonably flat samples. The height information extracted by the parallel interferometer detection system 14 represents the true instantaneous height of the probe, rather than the output of a Z actuator servo control loop as utilized in conventional SPM. However, the SPM controller 3 is used to maintain the probe array within a suitable range of the surface over longer time periods. This is achieved by processing the height data for each probe to extract a parameter that is indicative, for example, of the dwell time of the probe tip on the surface. Other parameters could be employed. These parameter values for each probe are then processed and used to drive a relatively slow z actuation control loop which adjusts the signal 58, the sole purpose of which is to maintain probe motion within set limits.

Optionally the microscope of FIG. 1 also has an optical system for generating an image of the beamlets on the probes, which will now be described. An illumination source 62 generates an illumination beam 63 which illuminates the probes via beam splitters 64, 65 (such as dichroic mirrors) and the objective lens 18. The beamsplitter 65 transmits the beamlets 15*a-c* but reflects the illumination beam 63 which has different wavelengths to the beamlets 15*a-c*.

Reflected light from the probes is directed onto a charge coupled device (CCD) camera 66 by a tube lens 67. The CCD camera 66 generates an image of the complete array of probes (similar to FIG. 6) which is input to the controller 3. The image can then be used by the controller 3 to adjust the XY position of the array of probes and/or the angles of the beamlets from the SLMs 12,51 so that the beamlets are positioned as required on the probes prior to imaging (for instance in the centre of the probe or at one edge). Once the beamlets have been crudely positioned on the probes using the image from the CCD camera 66, the controller 3 can then use the signals from the interferometer photodiode 22 to adjust the XY position of the array of probes and/or the angles of the beamlets from the SLMs 12,51 so that the beamlets are accurately positioned on the probes. This is done by moving the beamlet or the probe to the left side of the probe until the beamlet falls off the left edge of the probe (and the associated signal from the photodiode changes abruptly or drops below a pre-set level); then moving the beamlet or the probe to the right side of the probe until the beamlet falls off the right edge of the probe (and the associated signal from the photodiode changes abruptly or drops below a pre-set level). The beamlet or probe can then be moved to the midpoint between these points, or some other desired position. A similar process can be used to accurately position the beamlets relative to the distal end of the cantilever.

This accurate xy alignment can be achieved by moving the probes in unison by moving the probe support 7, or more preferably by independently adjusting the angles of the beamlets from the SLMs 12,51 by operation of the control signals 58.

Figure 7:
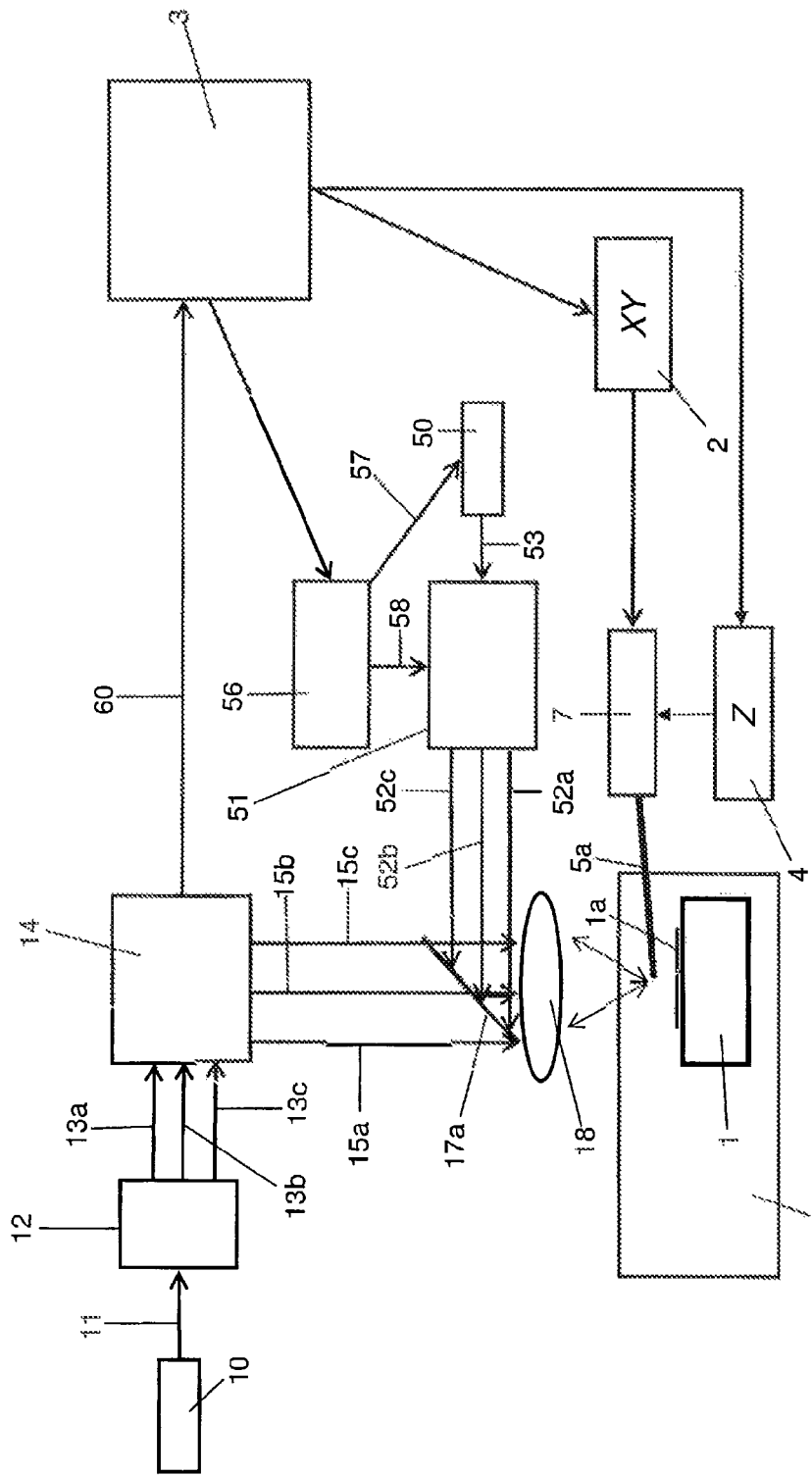
FIG. 7 is a schematic drawing of a biosensor.

A microcantilever biosensor will now be described with reference to FIG. 7. Many of the components are equivalent to those shown in FIG. 1, and the same reference numbers will be used for such equivalent components. However there is no requirement for probe array scanning, and the probe array is housed within a microfluidic cartridge 70 with an optical port that is capable of delivering the fluid to be analysed to the probe array while allowing optical access. It will be appreciated that such microfluidic systems are well known in the art and so will not be described further here. Tracking mirror 17 from FIG. 1 is omitted and replaced by a fixed angled dichroic mirror 17*a*.

The probe array could be comprised of silicon or silicon nitride cantilevers as described above, except that no tip is necessary, as the active biosensor area of the cantilever is generally a well-defined area on the cantilever back, rather than on the tip. An area on the back of the cantilever will therefore be coated with a bimetallic layer for photothermal actuation, while another segment will typically be coated with gold for the biosensor, generally well away from both the actuation and detection lasers to avoid photodegradation. Gold is often used because it is suitable for the immobilization of thiol modified biochemical entities. These are the receptors which bind the target molecules (ligands) to the biosensor surface, thereby inducing surface stress and increasing the mass of the probe overall. It will be appreciated that many receptor-ligand combinations exist and are well known in the art, and so will not be described in detail here. The exact number of probes in the array also varies depending on the biosensor application, because clinical applications often have multiple target molecules. Typically arrays might consist of 10's or 100's of cantilevers, including both active and reference cantilevers. Reference cantilevers are typically used for temperature compensation during microfluidic operation and analyte measurement.

The cantilever probe array and microfluidic system 70 is incorporated into the parallel interferometer and photothermal actuation system in much the same way as the SPM of FIG. 1. The biosensor array can be operated in either static or dynamic modes as described above. The dynamic mode will be described below in more detail.

In the dynamic mode the increase of mass of each probe produces a reduction in the resonant frequency that can be used to record the presence and concentration of the ligand in the microfluidic cavity surrounding the array. The parallel biosensor system is configured with the probe array suitably functionalized and aligned within the interferometer 14, with beamlets positioned on each cantilever by the SLMs 12,51 to actuate and detect motion of the probes. In this case each probe is designed and fabricated to have the same resonant frequency, although some small variation is inevitable and not critical to the system operation. The analyte fluid is introduced into the microfluidic system 70 and is typically pumped to the probe array cavity for analysis, or driven by capillary action.

In order to sense the resonant frequency shift that takes place as the ligands bind to the receptors, the signal 57 initially drives the IR laser 50 at a frequency close to the unbound resonant frequency of the probe array. In the case considered here the drive frequency is below resonance, situated in a region of the resonant curve where the amplitude of probe oscillation varies approximately linearly with frequency. For any given probe, the new probe resonant frequency begins to drop as the ligand is bound, bringing the probe resonant frequency closer to the photothermal drive frequency. As a consequence the amplitude of the probe oscillation increases, approximately linearly with the bound mass of the ligands. Alternative detection schemes based on phase sensitive operation are known in the art and so will not be described here. It will be appreciated that the simplified description given above could be amplified to take into account many of the more detailed considerations, such as compensation schemes and calibration, that are necessary for successful biosensor operation. Such details fall outside the scope of this application and are well known in the art.

The parallel interferometric detection and actuation scheme described above offers many advantages for biosensor operation. Clinical applications often require multiple targets and hence probes, making conventional PSD detection impractical. The inventive system could in principle be scaled to several 100's of probes, this covering many clinical diagnostic requirements. The parallel interferometric detection and actuation system is also flexible, and can be reconfigured by re-programming the controller 3 to operate with biosensor arrays of different dimensions and characteristics. The probe array itself is simple, cheap and disposable which is essential for many applications. The probe array, typically integrated into a microfluidic cartridge 70, can be introduced into the system quickly and the alignment completely automated as the beamlets can be directed under computer control by the SLMs until the required optimum detection and photothermal actuation conditions are reached.

Figure 8:
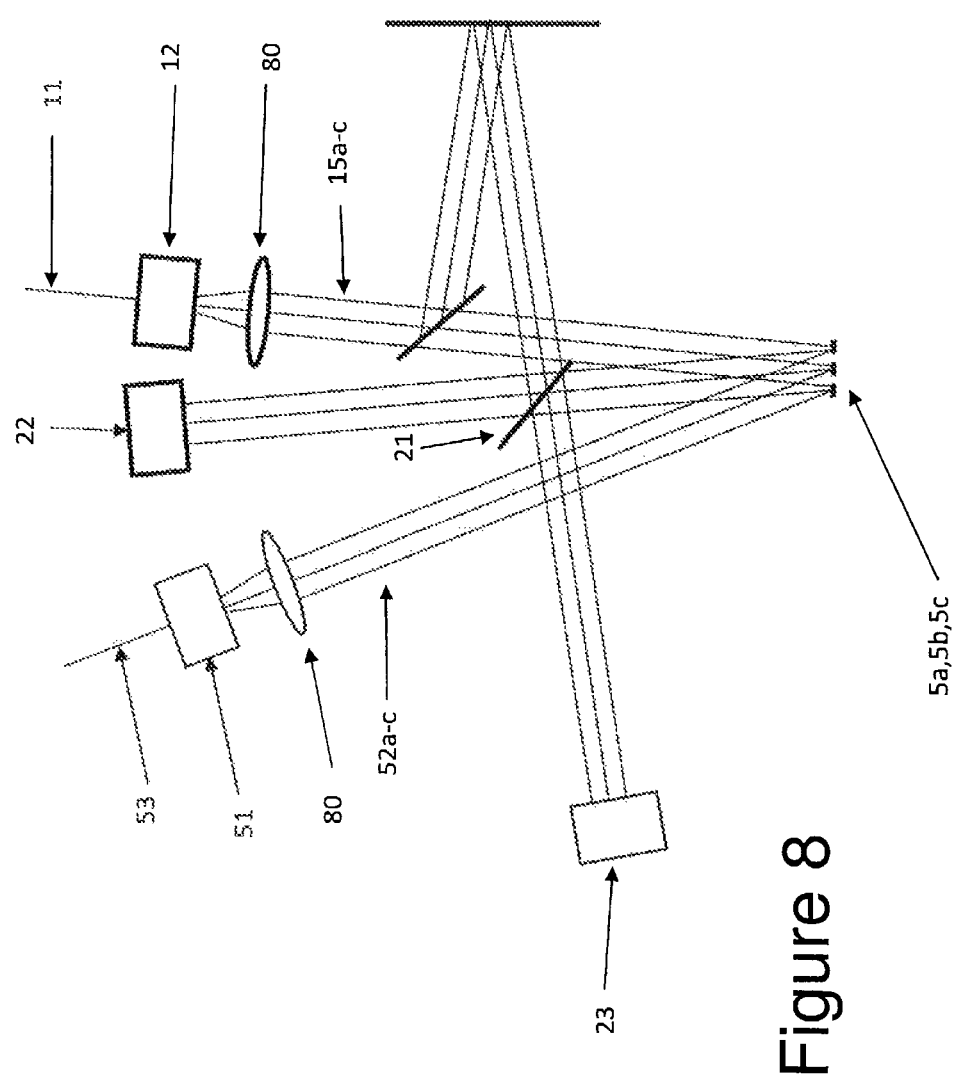
FIG. 8 shows an embodiment in which no objective lens is used and the beamlets are parallel as the illuminate the probes.

In the embodiments of the invention described above, an objective lens 18 is used to direct the sensing and actuation beamlets onto the probes. However, the use of an objective lens is not essential and FIG. 8 shows an embodiment in which no objective lens is used. The embodiment of FIG. 8 has various elements in common with the embodiment of FIG. 1, and the same reference numbers are used for these elements. A lens or additional optical component is used to produce a desired beamlet configuration. In this case a lens 80 is used after each DOE 12, 51 to generate a parallel array of beamlets which are also parallel as they illuminate the probes. Note that a lens (not shown) could be provided in front of each of the photodiodes 22, 23 to partially focus the beamlets onto the photodiode, for example to match spot spacing with photodiode geometry. The photodiodes 22, 23 would not be placed in the focal plane of their respective lens as the beamlets are parallel and would be focused to a single spot at the focal plane of the lens.

Figure 9:
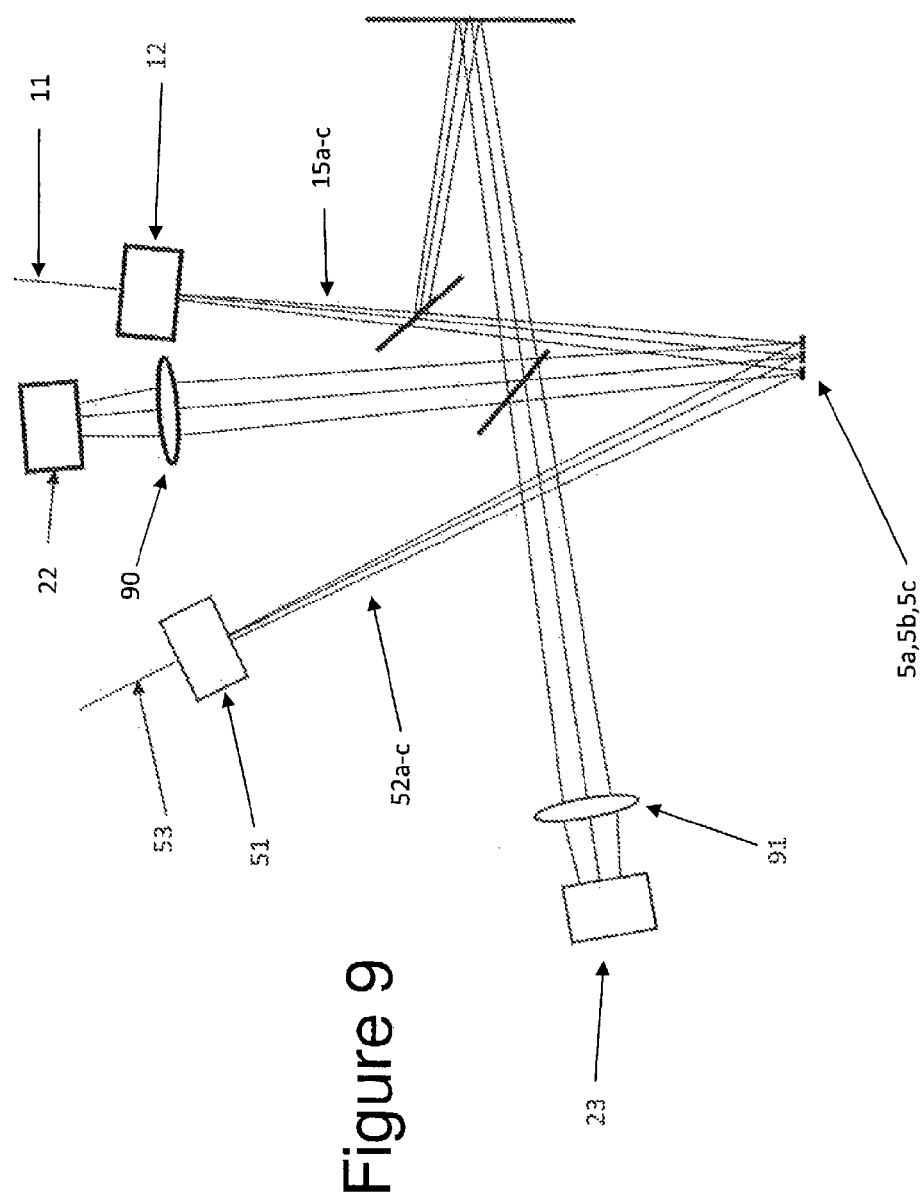
FIG. 9 shows an embodiment in which no objective lens is used and the beamlets are not parallel as the illuminate the probes.

FIG. 9 shows another embodiment with no objective lens. In this case there are also no lenses 80 after the DOEs 12, 51, so the beamlets illuminating the probes are not parallel. Lenses 90,91 are shown in front of the photodiodes 22, 23.

Although the invention has been described above with reference to one or more preferred embodiments, it will be appreciated that various changes or modifications may be made without departing from the scope of the invention as defined in the appended claims.

The invention claimed is:

1. A method of detecting the positions of a plurality of probes, the method comprising:
    a. directing an input beam into an optical device;
    b. transforming the input beam with the optical device into a plurality of output beamlets;
    c. splitting each output beamlet into a sensing beamlet and an associated reference beamlet;
    d. simultaneously directing each of the sensing beamlets onto an associated one of the probes to generate a reflected beamlet;
    e. combining each reflected beamlet with its associated reference beamlet to generate an interferogram; and
    f. measuring each interferogram to determine the position of an associated one of the probes.

2. The method of claim 1 further comprising: directing a second input beam into a second optical device; transforming the second input beam with the second optical device into a plurality of actuation beamlets; simultaneously directing each of the actuation beamlets onto an associated one of the probes, wherein each probe is arranged such that when the probe is illuminated by its respective actuation beamlet it deforms; and modulating the intensity of the second input beam over time in order to modulate the intensity of the actuation beamlets and thus modulate the positions of the probes relative to a sample.

3. The method of claim 1 wherein combining each reflected beamlet with its associated reference beamlet to generate an interferogram comprises directing each reflected beamlet with its associated reference beamlet onto a sensor with a sensor lens, and wherein the sensor measures each interferogram to determine the position of an associated one of the probes.

4. The method of claim 1 further comprising operating the optical device with a control signal in order to modulate an angle of one or more of the output beamlets over time.

5. The method of claim 1 wherein the optical device transforms the input beam by diffraction.

6. The method of claim 1 wherein the optical device imposes a spatially varying phase or amplitude modulation on the input beam.

7. The method of claim 1 wherein the plurality of probes comprises ten or more probes.

8. Apparatus for detecting the positions of a plurality of probes, the apparatus comprising: an optical device arranged to transform an input beam into a plurality of output beamlets; one or more beam splitters arranged to split each output beamlet into a sensing beamlet and an associated reference beamlet and simultaneously direct each of the sensing beamlets onto an associated one of the probes to generate a reflected beamlet; and one or more sensors arranged to measure inteferograms which are generated by combining each reflected beamlet with its associated reference beamlet to determine the positions of the probes.

9. The apparatus of claim 8 wherein the optical device transforms the input beam by diffraction.

10. The method of claim 1 further comprising modulating the positions of the probes relative to a sample in accordance with the positions of the probes determined by measuring the interferograms.

11. The method of claim 1, wherein the output beamlets are not parallel with each other.

12. The method of claim 1, wherein an objective lens is arranged to simultaneously direct each of the sensing beamlets onto an associated one of the probes.

13. The method of claim 1, wherein the probes are used for scanning probe microscopy, biosensing, nanolithography, or data storage.

14. The apparatus of claim 8, wherein the output beamlets are not parallel with each other.

15. The apparatus of claim 8, wherein an objective lens is arranged to simultaneously direct each of the sensing beamlets onto an associated one of the probes.

16. The apparatus of claim 8, wherein the probes are scanning probe microscopy probes, biosensing probes, nanolithography probes, or data storage probes.

* * * * *